United States Patent [19]

McGovern et al.

[11] Patent Number: 4,877,607

[45] Date of Patent: Oct. 31, 1989

[54] **ATTRACTANTS FOR *DACUS LATIFRONS*, THE MALAYSIAN FRUIT FLY**

[75] Inventors: Terrence P. McGovern, Bowie, Md.; Robert A. Flath, Kensington, Calif.; Roy T. Cunningham, Hilo, Hi.

[73] Assignee: The United States of America as represented by the Secretary of Agriculture, Washington, D.C.

[21] Appl. No.: 247,546

[22] Filed: Sep. 22, 1988

[51] Int. Cl.$^4$ .............................................. A01N 25/00
[52] U.S. Cl. ................................................... 424/84
[58] Field of Search .......................................... 424/84

[56] References Cited

U.S. PATENT DOCUMENTS 2,974,086  3/1961  Berzoa et al. ..................... 424/84

OTHER PUBLICATIONS

Qureshi et al., Pakistan J. Sci. Ind. Res., vol. 19, No. 1 (Feb. 1976).
L. F. Steiner, "Methyl Eugenol as an Attractant for Oriental Fruit Fly," *Journal of Economic Entomology* 45: 241–245 (1952).
W. F. Barthel, N. Green, I. Keiser, and L. F. Steiner, "Anisylacetone, Synthetic Attractant for Male Melon Fruit Fly," *Science* 126: 654 (1957).
B. H. Alexander et al., "The Development of Male Melon Fly Attractants," *Agricultural and Food Chemistry* 10: 270–276 (1962).

*Primary Examiner*—Douglas W. Robinson
*Assistant Examiner*—Roger Gobrogge
*Attorney, Agent, or Firm*—M. Howard Silverstein; John D. Fado; Margaret A. Connor

[57] ABSTRACT

Certain cyclohexyl and cyclohexenyl aliphatic alcohols and ketones are potent attractants for *Dacus latifrons*, the Malaysian fruit fly. By attracting adult males to field traps, the compounds provide a means for detecting, monitoring, and controlling this agricultural pest.

11 Claims, No Drawings

ATTRACTANTS FOR *DACUS LATIFRONS*, THE MALAYSIAN FRUIT FLY

BACKGROUND OF THE INVENTION

1. Field of the Invention

This invention relates to novel attractants for the Malaysian fruit fly. More particularly, the invention relates to certain cyclohexyl and cyclohexenyl aliphatic alcohols and ketones that are potent attractants for the Malaysian fruit fly.

2. Description of the Art

*Dacus latifrons* (Hendel), known as the Malaysian fruit fly, is a fruit and vegetable infesting tephritid fruit fly. It is found in Taiwan, Malay Peninsula, Thailand, and Laos. In 1983, the Malaysian fruit fly was discovered in Hawaii where pepper, *Capsicum annum* L., was found to be its prime host. It is not presently known to occur in the mainland United States. However, its normal breeding hosts are in the solanaceous group of plants making the western and southern U.S. vegetable industry particularly susceptible to *D. latifrons*.

With travel and foreign trade, the possibility of accidentally importing the Malaysian fruit fly from Hawaii or elsewhere is of concern to the agricultural community. What is needed is an effective lure to detect quickly any flies that may gain entry and become established.

No male attractants are known for the Malaysian fruit fly. Male attractants for some Dacus species have been reported. Steiner (*Journal of Economic Entomology* 45: 241-248 (1952)) reported that methyleugenol (4-allyl-1,2-dimethoxybenzene) was extremely attractive to the male oriental fruit fly, *Dacus dorsalis* Hendel. Barthel and co-workers (*Science* 126: 654 (1957)) reported that anisylacetone [4-(p-methoxyphenyl)-2-butanone] was an effective lure for the male melon fly *Dacus cucurbitae* Coquillett. Alexander et al. (*Agricultural and Food Chemistry* 10: 270-276 (1962)) investigated compounds related to anisylacetone for effectiveness as attractants for the male melon fly. Of the 3000 compounds screened, the most attractive compounds overall were derivatives of 4-phenyl-2-butanone. The best attractant was found to be cue-lure [4-(p-acetoxyphenyl)-2-butanone]. The Malaysian fruit fly responds only weakly to methyleugenol and does not respond to cue-lure. Thus, male lures are not available to detect or control this species.

SUMMARY OF THE INVENTION

We have discovered that certain cyclohexyl and cyclohexenyl aliphatic alcohols and ketones are potent attractants for the Malaysian fruit fly. These compounds are characterized by the structural formula

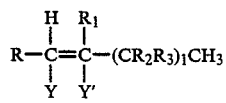 (A)

wherein
= represents a single or double bond and Y and Y' form the carbon-carbon double bond joining the positions to which they are attached if = is a double bond and Y and Y' are each hydrogen if = is a single bond;
$R_1$ is H or $CH_3$;
$R_2$, $R_3$ is selected from H, OH; or =O; and
R is selected from:

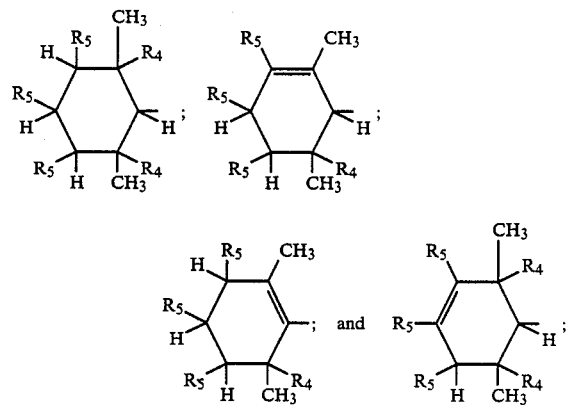

wherein
$R_4$ is H or $CH_3$,
$R_5$ is H or $CH_3$, with the proviso that only one $R_5$ on the ring is $CH_3$, and
wherein when Y and Y' are H and $R_2R_3$ is =O, then R is cyclohexenyl.

The compounds of the invention are the first known chemical attractants for this species of Dacus fruit flies. An important feature of these attractants is that they attract males of the species and thus are useful for male annihilation. When used in combination with a fruit fly insecticide or other control agent, the compounds can be used to attract and kill male Malaysian fruit flies before they are able to fertilize the females.

As discussed above, an efficient detection system is needed to detect an incipient invasion of the Malaysian fruit fly onto the continental U.S. or other areas of the world that may be threatened. The attractants of the invention provide, for the first time, a means to detect, monitor, or control this species of fruit flies. The effectiveness of these compounds in attracting *D. latifrons* males suggests the following economic applications: (1) the detection of infestation outbreaks; (2) the monitoring of existing adult populations in order to predict future infestation levels for scheduling treatment with conventional pesticides; and (3) the control of reproduction in adult populations by attracting a demographically significant portion of the male population for subsequent destruction or sterilization.

In accordance with this discovery, it is an object of the invention to define a group of compounds possessing activity as Malaysian fruit fly attractants.

Another object of the invention is to provide attractants for Malaysian fruit fly males as survey, detection, monitoring, or control agents for this agricultural pest.

A further object is to provide Malaysian fruit fly attractants, for use with insecticides, biological control agents or other toxicants to attact and combat the pest.

Other objects and advantages of the invention will become readily apparent from the ensuing description.

DETAILED DESCRIPTION OF THE INVENTION

Contemplated for use in this invention as attractants for Malaysian fruit fly males are alicyclic substituted aliphatic alcohols and ketones as defined by the structural formula A, above. As shown in formula A, members of this group contain a linear aliphatic chain which may be hydroxylated or ketonized and may be saturated or α,β-unsaturated. The compounds are characterized by possessing a methyl substituted cyclohexane or cyclohexene ring located at the end of the chain. As noted above in the "Background of the Invention," those compounds previously identified as potent attractants for other Dacus species, e.g., methyleugenol and cuelure, possess a benzene ring. In contrast, the compounds of the invention do not have a benzene ring but contain a cyclohexyl or cyclohexenyl moiety. Further, the attractants of the invention have at least two methyl substituents on the ring; in contrast, none of the prior art attractants for other Dacus species possess methyl substituents on the benzene ring. Thus, there is no suggestion in the prior art of a structural/functional relationship of the compounds of the invention as attractants for *D. latifrons*. Further, the activity of the compounds of the invention is not shared by closely related compounds. For example, α and β ionyl acetates; 4-(2,6,6-trimethyl-2-cyclohexen-1-yl)-2-methyl-3-buten-2-ol; 5-(2,6,6-trimethyl-2-cyclohexen-1-yl)-4-methyl-4-penten-3-ol; 5-(2,6,6-trimethyl-1-cyclohexen-1-yl)-3-penten-2-ol; 4-(6-methyl-3-cyclohexen-1-yl)-3-buten-2-ol; 4-(cyclohexan-1-yl)-3-buten-2-ol; 4-(3-cyclohexen-1-yl)-3-buten-2-ol; tetrahydroionone; dimethylionone, and β-ionone are unattractive or very weakly attractive to *D. latifrons*.

The compounds of the invention may be used as a detecting agent, monitoring agent, or control agent for adult male Malaysian fruit flies. In practice, the compound is used as a trap bait or is otherwise applied to a locus of adults in an effective attractant amount. An effective amount is defined as that quantity of compound which attracts Malaysian fruit fly adult males to the location of a bait at a rate significantly higher than males are attracted to a location baited with methyleugenol. Factors such as insect population density, temperature, wind velocity, release rate, and method of application will influence the actual number of flies attracted. The amount of compound that will be effective in a particular set of circumstances can be readily determined by a dose response field test. When used as a survey detection tool on cotton wicks in a trap, amounts of about 4 to 6 ml/trap are effective.

It is envisioned that the compounds of the invention would be effective in detecting, monitoring or controlling Malaysian fruit fly populations when used in conjunction with any type of trap or attractant disseminator known in the art. Illustrative of such a trap is the Jackson trap. Exemplary of disseminators are a cotton wick or a plastic matrix copolymer. Typically, the compound would be applied to the release substrate undiluted or in solution with a suitable liquid carrier such as acetone or ethyl alcohol. The compound can also be incorporated into a composition comprising a suitable solid carrier or substrate such as clay, vermiculite, cellulose and the like. The release rate can also be controlled by any of the various encapsulation techniques as known in the art.

When used as a detection or monitoring agent, traps are baited with the compounds of the invention and the catch tabulated to determine size and location of infestation. Economic use of appropriate pest management systems can then be determined.

The invention finds particular use for annihilation of male Malaysian fruit flies. Use of the attractants of the invention as a control agent can be carried out in several ways. One method is to use the compound to attract the insects to suitable substrates and subsequently or simultaneously expose the insects to insecticides which control the Malaysian fruit fly. An effective amount of the insecticide is used, that is, an amount that is lethal for an exposed insect or at least sublethal but sufficient to incapacitate the insect in regard to mating activity. Illustrative of the wide variety of insecticides which may be used with the compound of the invention are naled and malathion. Insecticides can be used in traps baited with the novel attractants of the invention. This eliminates the need to spread the insecticides unnecessarily and helps prevent killing useful insects and other animals.

A second method to control Malaysian fruit flies using the compounds is to detect the location and boundaries of localized Malaysian fruit fly infestations and employ in the area biological control agents. As with the use of insecticides, this method eliminates the need to spread the control agents unnecessarily and minimizes adverse impact to useful insects and the environment.

It is within the compass of the invention to use a single attractant compound as herein described or mixtures of two or more of these compounds.

The compounds of the invention may be categorized further as follows:

Group I. Cyclohexyl and cyclohexenyl butenols of the structure

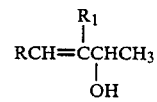

wherein R and $R_1$ are as defined above.

Group II. Cyclohexyl and cyclohexenyl butanols of the structure

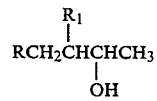

wherein R and $R_1$ are as defined above.

Group III. Cyclohexyl and cyclohexenyl butenones of the structure

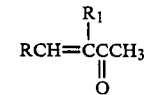

wherein R and $R_1$ are as defined above.

Group IV. Cyclohexenyl butanones of the structure

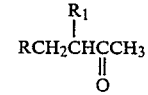

wherein R and $R_1$ are as defined above.

Typical examples of the compounds which may be used in the method of the invention are the following:

Group I. 4-(2,6,6-Trimethyl-2-cyclohexen-1-yl)-3-buten-2-ol(α-ionol); 4-(2,6,6-trimethyl-1-cyclohexen-1-yl)-3-buten-2-ol(β-ionol); 3-methyl-4-(2,6,6-trimethyl-2-cyclohexen-1-yl)-3-buten-2-ol(α-methyl-α-ionol); 4-

(2,4,6-trimethyl-3-cyclohexen-1-yl)-3-buten-2-ol; and 4-(2,5,6,6-tetramethyl-2-cyclohexen-1-yl)-3-buten-2-ol.

Group II. 4-(2,6,6-Trimethylcyclohexyl)-2-butanol(tetrahydroionol); 4-(2,4,6-trimethylcyclohexyl)-2-butanol; and 4-(2,6,6-trimethyl-2-cyclohexen-1-yl)-2-butanol(dihydro-α-ionol).

Group III. 4-(2,6,6-Trimethyl-2-cyclohexen-1-yl)-3-buten-2-one(α-ionone); and 4-(2,5,6,6-tetramethyl-2-cyclohexen-1-yl)-3-buten-2-one(α-irone).

Group IV. 4-(2,6,6-Trimethyl-2-cyclohexen-1-yl)-2-butanone(dihydro-α-ionone).

Many of the attractants of the invention are available from commercial sources. If not so available, they can be made by synthetic procedures known to those in the art as described below.

The compounds of Groups I and II may be prepared from the corresponding ketones by reducing the keto group to a hydroxy group using a suitable reducing agent such as sodium bis(2-methoxyethoxy)aluminum hydride. For example, α-ionol can be prepared by reacting α-ionone with the aforementioned reducing agent. This is described in detail below in Example 2.

The compounds of Group III and the ketone precursors of Groups I and II may be prepared as follows:

Cyclohexenyl compounds having a double bond in the 1 or 2 positions on the ring are prepared from pseudoionone (6,10-dimethyl-3,5,9-undecatriene-2-one) which is available commercially or can be prepared by the condensation of citral and acetone.

To prepare the cyclohexenyl ketones having a double bond in the 1 position, pseudoionone is reacted with a cyclizing agent, e.g., a mixture of concentrated sulfuric acid and glacial acetic acid, which produces β-ionone. The product is separated by standard techniques. This procedure is described in detail below in Example 1.

To prepare the cyclohexenyl ketones having a double bond in the 2 position, pseudoionone is reacted with a cyclizing agent such as phosphoric acid which produces α-ionone. See Example 1 below.

Variously substituted 2-cyclohexen-1-yl or 1-cyclohexene-1-yl ketones are prepared by selecting the appropriately substituted pseudionone and treating as described above. 3-Cyclohexenyl ketones are prepared by reacting a suitable 3-cyclohexenylcarboxaldehyde, that is obtained from a Diels-Alder reaction between an appropriately substituted butadiene and crotonaldehyde, with an appropriate condensation reagent to provide the desired 4-(3-cyclohexen-1-yl)-3-buten-2-ones. See Example 1 below.

Similarly, the cyclohexyl ketones are prepared by reacting a suitable cyclohexanecarboxaldehyde with an appropriate condensation reagent to provide the desired 4-(cyclohexyl)-3-buten-2-ones. See Example 1 below.

Group IV compounds are prepared by treating the corresponding ketones to selectively reduce either the α,β-olefin in preference to the other olefin and the carbonyl group or both olefins in preference to the carbonyl group.

The following examples are intended only to further illustrate the invention and are not intended to limit the scope of the invention which is defined by the claims.

EXAMPLE 1

Synthesis of Ketone Compounds

Synthesis of β-Ionone. The cyclizing agent [35 g of conc. sulfuric acid (95%) and 15 g of glacial acetic acid] was placed in a 250 ml three-necked flask with a mechanical stirrer, a dropping funnel, and a thermometer reaching into the reaction mixture. The flask was cooled in an ice bath and the cyclizing agent was vigorously stirred while pseudoionone (10 g) was added dropwise during 15–20 minutes; the rate of addition was adjusted so that the temperature of the reaction mixture did not exceed 10° C. After addition, the cooling bath was removed and stirring was continued at 10°–15° C. for 5–10 minutes. The reaction mixture was poured into a mixture of ice and water (200 g) and ether (100 ml) with vigorous stirring. The water layer was again extracted with ether and the combined ether extracts were washed with water, sodium carbonate solution (1%), then to neutral with water and dried over anhydrous magnesium sulphate. After the removal of ether, the residue was distilled under reduced pressure. β-Ionone (5.1 g) was obtained as a pleasant smelling light yellow colored liquid; boiling point 73° C./0.25 mm; $n_D^{25}$ 1.5164.

Synthesis of α-Ionone. The same procedure was used as for β-ionone except phosphoric acid was used as the cyclizing agent. Boiling point 63°–65° C./0.1 mm; $n_D^{25}$ 1.4960; yield 3.8 g.

Preparation of Other α-Ionones. By proper selection of a pseudoionone and cyclization agent other compounds of Group III can be synthesized. α-Irone (4-(2,5,6,6-tetramethyl-2-cyclohexen-1-yl)-3-buten-2-one) has the following constants: boiling point 86°–87° C./0.5 mm, $n_D^{25}$ 1.4987; yield 77%. Data was taken from Kimel et al., *Journal of Organic Chemistry* 22: 1611–1618 (1957).

Syntheses of 4-(3-Cyclohexen-1-yl)-3-buten-2-one. 1-Triphenylphosphoranylidene-2-propanone (0.02 mole, 6.4 g) and 50 ml of dried benzene or toluene were placed in a dry, nitrogen flushed 250 ml two-necked round bottom flask equipped with a condenser mounted on top of a water separater and a magnetic stirrer. The mixture was refluxed to remove any water contaminant. After cooling, 2.5 ml of freshly distilled 3-cyclohexene-1-carboxaldehyde (0.02 mole), obtainable from commercial sources or from a Diels-Alder reaction between butadiene and acrolein, was added dropwise. The reaction mixture was maintained under a nitrogen atmosphere, stirred magnetically, and brought to reflux which was continued for 45 hours. The cooled reaction mixture was poured into water and extracted 5 times with hexane. The combined hexane extracts were washed with water, dried over anhydrous magnesium sulfate and filtered. The solvent was removed and the residue was distilled under reduced pressure. The product (2.9 g) was collected at 118° C./20–25 mm, $n_D^{25}$ 1.4979.

Preparation of other 4-(3-cyclohexen-1-yl)-3-buten-2-ones included 4-(6-methyl-3-cyclohexen-1-yl)3-buten-2-one [b.p. 54° C./0.2 mm; $n_D^{25}$ 1.4932; 57% yield]; 4-(2,4,6-trimethyl-3-cyclohexen-1-yl)-3-buten-2-one [b.p. 72° C./0.2 mm; $n_D^{25}$ 1.4908; 54% yield]; 4-(3,4-dimethyl-3-cyclohexene-1-yl)-3-buten-2-one [b.p. 70°–71° C./0.1 mm; $n_D^{25}$ 1.5005; 51% yield].

Synthesis of 4-Cyclohexyl-3-buten-2-one. Freshly distilled cyclohexanecarboxaldehyde (0.04 mole, 5 ml) was subjected to the same condensing agent and procedure that was described in the previous example with 3-cyclohexene-1-carboxaldehyde. The reflux period was 113 hours [b.p. 49° C./0.2 mm; $n_D^{25}$ 1.4820; 63% yield].

Synthesis of Cyclohexenyl Butanones. The cyclohexenylbutanones are synthesized by selectively hydrogenating the α,β-conjugated olefin in the α-ionones over palladium in a basic medium (0.3N alcoholic potassium hydroxide) at room temperature and atmospheric pressure in preference to the isolated double bond. Physical constants for 4-(2,6,6-trimethyl-2-cyclohexen-1-yl)-2-butanone[b.p. 67°–69° C./0.4 mm; $n_D^{25}$ 1.4371].

EXAMPLE 2

Synthesis of Groups I and II Compounds

Group I and II compound are prepared from the corresponding ketones by reducing the keto group to a hydroxyl group using a suitable reducing agent such as sodium bis(2-methoxyethoxy)aluminum hydride.

Synthesis of α-Ionol. 7.4 ml of 3.4M (0.025 mole) sodium bis(2-methoxyethoxy)aluminum hydride (sold under the trade name "Red-Al" by Aldrich Chemical Co., Milwaukee, WI) diluted with 20 ml of benzene was added dropwise to a solution of α-ionone in 50 ml of benzene contained in a dry 500 ml three-necked flask equipped with a condenser fitted with a drying tube. The flask was flushed with dry nitrogen and a slight nitrogen flow was maintained throughout the reaction.

After the addition was completed, the reaction mixture was refluxed for 2 hours. After cooling to room temperature the reaction complex was hydrolyzed by the addition of 50 ml of 20% sulfuric acid solution. The organic layer was separated and then neutralized by washing with dilute (5–10%) sodium carbonate solution. After drying, filtering, and removal of the solvent, the crude product was purified by fractional distillation; boiling point 61° C./0.15 mm; $n_D^{25}$ 1.4875, yield 6.6 g. The infrared spectrum and GC retention time was identical with commercially available α-ionol.

Synthesis of β-Ionol. β-Ionol was synthesized from β-ionone as described above for synthesis for aα-ionol with the following modification: 20% sodium hydroxide solution was used to hydrolyze the reaction complex in place of the sulfuric acid solution and the separated organic layer was neutralized by washing with water. α-Ionol thus prepared had the following constants: boiling point, 78° C./0.2 mm; $n_D^{25}$ 1.4975; yield 5.9 g. Infrared spectrum and GC retention time was identical to that of a commercially available sample.

Synthesis of Other Alcohols. The following compounds were prepared from the corresponding ketones by the method described above for α-ionol and had the following constants: 3-methyl-4-(2,6,6-trimethyl-2-cyclohexen-1-yl)-3-buten-2-ol(α-methyl-α-ionol), b.p. 87° C./0.2 mm; $n_D^{25}$ 1.4907; 77% yield; 4-(2,6,6-trimethylcyclohexyl)-2-butanol (tetrahydroionol), b.p. 72°–3° C./0.1 mm; $n_D^{25}$ 1.4707; 73% yield; 4-(2,4,6-trimethyl-3-cyclohexen-1-yl)-3-buten-2-ol, b.p. 72°–3° C./0.15 mm; $n_D^{25}$ 1.4849; 84% yield; 4-(2,5,6,6-tetramethyl-3-cyclohexen-1-yl)-3-buten-2-ol, b.p. 78° C./0.15 mm; $n_D^{25}$ 1.4893; 57% yield; 4-(2,4,6-trimethylcyclohexyl)-2-butanol, b.p. 78° C./ 0.25 mm; $n_D^{25}$ 1.4750; 66% yield; and 4-(2,6,6-trimethyl-2-cyclohexen-1-yl)-2-butanol, b.p. 72° C./0.15 mm; $n_D^{25}$ 1.4797; 55% yield.

EXAMPLE 3

Attractancy Tests

Bioassay Procedure. The primary screening of compounds for attractant activity was done by preparing 0.1% solutions or emulsions of the test material in water (according to a standard test protocol). Forty microliters (or 0.04 grams in a solution of either acetone or ethyl alcohol for test compounds which are solids) were added to 2.0 ml of ethyl alcohol with 0.04 ml of emulsifying agent and this mixture was added to 40 ml of water. Twenty ml of these 0.1% solutions were put in the bottom of a glass invaginated fly trap (modified from a 500 ml boiling flask to have an invagination into the bottom) (M. McPhail, *Journal of Economic Entomology* 31: 758–761, 1939). Two traps of each treatment were placed on the horizontally rotating wheel (1.5 rpm) in a large Gow olfactometer (P. Gow, *Journal of Economic Entomology* 47: 153–160, 1954) (10 ft × 10 ft 8 ft high) and exposed to several thousand sexually mature *Dacus latifrons* flies which were reared in the laboratory. After from 0.5 to 3.0 hours exposure the traps were removed (usually 7 test compounds and one standard attractant were compared during any one run—two traps of each treatment). The captured flies were counted by sex. Promising compounds were selected out for further testing. In doing statistical analyses, the tests were replicated in time; that is, four or more test runs with new preparations and additional flies were done, usually on four different days. Methyleugenol or a protein bait (Steiner, *Journal of Economic Entomology* 45: 838–843 (1953)), considered to be weak attractants, were used as the standard of comparison in Tests A, B, and C. α-Ionol, which was found to be a strong attractant, was used as the standard of comparison in tests D and E.

Test A. The first very strong male attractant property was discovered in our test run on Aug. 20, 1987. The results are shown in Table 1. As can be seen from Table 1, the compounds of the invention are potent attractants for Malaysian fruit fly males.

TABLE 1

|  | Total Catch of *D. Latifrons* in 2 Traps | |
|---|---|---|
|  | Males | Females |
| Methyleugenol (standard)[a] | 85 | 3 |
| Vanillin[a] | 19 | 21 |
| 3,4-Dimethoxyacetophenone[a] | 4 | 14 |
| α-Ionol | 241 | 8 |
| β-Ionol | 356 | 7 |
| Methyl-Ionol | 198 | 4 |
| 4-Hydroxy-3-methyl-2-(2-pentenyl)-2 cyclopentene-1-one[a] | 34 | 1 |
| (−)-Carvone[a] | 41 | 2 |

[a] Not in accordance with the invention; included for comparison purposes.

Test B. Table 2 below shows test data obtained for six compounds of the invention using the bioassay procedure described above. Methyleugenol was the standard.

TABLE 2

|  | Catch of Male *D. Latifrons*[a] | | | | |
|---|---|---|---|---|---|
|  | Replicates | | | | Weighted Mean |
| Compound | 1 | 2 | 3 | 4 | Catch[b] |
| β-Ionol | 262 | 255 | 221 | 154 | 220.75a |
| α-Ionol | 166 | 188 | 238 | 210 | 119.59a |
| α-Ionone | 180 | 175 | 146 | 128 | 156.50b |
| α-Irone | 126 | 114 | 99 | 99 | 109.20c |
| α-Methyl-α-Ionol | 124 | 121 | 93 | 82 | 104.19c |
| Tetrahydroionol | 109 | 97 | 98 | 93 | 99.15c |
| Methyleugenol (standard) | 68 | 87 | 55 | 66 | 68.52d |

[a] Test period varied from 2 to 3 hours.
[b] Catches followed by the same letter within a column are not significantly different at the 5% level (Duncan's multiple range test).

Test C. Table 3 below shows data obtained for compounds of the invention using the bioassay procedure described above. A protein bait was used as the standard.

TABLE 3

| Compound | Catch/replicate | | | | | | | | | | | | Totals | | |
| --- | --- | --- | --- | --- | --- | --- | --- | --- | --- | --- | --- | --- | --- | --- | --- |
| | 1 | | | 2 | | | 3 | | | 4 | | | Weighted mean catch[a] | | |
| | ♂ | ♀ | Total | ♂ | ♀ | Total | ♂ | ♀ | Total | ♂ | ♀ | Total | ♂ | ♀ | Total |
| α-Ionol | 451 | 7 | 458 | 173 | 4 | 177 | 175 | 2 | 177 | 232 | 2 | 234 | 247a | 3b | 251a |
| β-Ionol | 377 | 8 | 385 | 130 | 4 | 134 | 237 | 10 | 247 | 161 | 3 | 164 | 217ab | 6b | 223ab |
| α-Ionone | 318 | 5 | 323 | 208 | 9 | 217 | 157 | 3 | 160 | 180 | 2 | 182 | 212ab | 4b | 216ab |
| Tetrahydroionol | 250 | 10 | 260 | 124 | 6 | 130 | 141 | 7 | 148 | 117 | 2 | 119 | 154bc | 6b | 160bc |
| 4-(2,4,6-Trimethyl-3-cyclohexen-1-yl)-3-buten-2-ol | 335 | 9 | 244 | 170 | 9 | 179 | 115 | 5 | 120 | 99 | 3 | 102 | 169bc | 6b | 157bc |
| 4-(2,5,6,6-Tetramethyl-2-cyclohexen-1-yl)-3-buten-2-ol | 234 | 6 | 240 | 82 | 5 | 87 | 140 | 8 | 148 | 87 | 7 | 94 | 129c | 6b | 136c |
| Standard (food bait) | 54 | 80 | 134 | 56 | 148 | 204 | 31 | 110 | 141 | 37 | 26 | 63 | 44d | 84a | 130c |

[a]Catches followed by the same letter within a column are not significantly different at the 5% level (Duncan's multiple range test).

Test D. Table 4 below shows tests data obtained for compounds of the invention using the bioassay procedure described above. α-Ionol, which was shown in earlier tests to be a potent attractant, was the standard.

TABLE 4

| Compound | Catch of Male D. Latifrons Weighted Mean Catch[a] |
| --- | --- |
| Dihydro-α-ionol | 120.50a |
| α-Ionone | 120.18a |
| α-Ionol (standard) | 101.25a |
| Dihydro-α-ionone | 79.25a |
| Tetrahydroionol | 79.03a |

[a] Catches followed by the same letter within a column are not significantly different at the 5% level (Duncan's multiple range test).

Test E. In another test, 4-(2,4,6-trimethylcyclohexyl)-2-butanol caught about 93% as many flies as the strong attractant α-ionol, indicating that it is a potent attractant.

EXAMPLE 4

Field Tests

A field test was carried out as follows: The test and control lures were tested in the field by hanging traps on trees in a macadamia nut orchard in Waimanalo, Oahu, Hawaii, and then releasing lab-reared sterile flies in an even fashion throughout the plot. Trees were spaced about 25 feet apart. A 10-replicate randomized complete block field plot design was used in laying out the traps. We had three treatments, two of which (A and B) were in standard survey Jackson traps (Harris, *Journal of Economic Entomology* 64: 62–65, 1971). The lures consisted of: A. 0.5 ml/wick in standard Jackson trap of methyleugenol+the insecticide naled (1%); B. 0.5 ml/wick in standard Jackson trap of α-ionol+naled (1%); and C. 50 ml/glass invaginated trap of solution of: Protein bait (9%)+borax (5%)+water (86%). The total catch during a 4-week period is shown in Table 5.

TABLE 5

| | D. latifrons | D. dorsalis |
| --- | --- | --- |
| A | 8 | 6,751 |
| B | 419 | 0 |
| C | 65 | 5 |

The *D. Dorsalis* catches were flies from a wild population while the *D. latifrons* catches were recovery of about 1% of the approximately 43,000 male *D. latifrons* which were released. This recovery rate compares favorably with what we would have expected from similar tests with the other male lures with their respective species.

It is understood that the foregoing detailed description is given merely by way of illustration and that modification and variations may be made therein without departing from the spirit and scope of the invention.

Having thus described our invention, we claim:

1. A method for attracting adult male Malaysian fruit flies, which comprises applying to the locus thereof an effective attractant amount of a compound having the structure

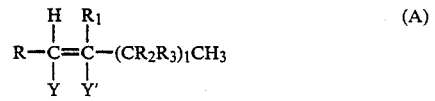

wherein $=$ represents a single or double bond and Y and Y' from the carbon-carbon double bond joining the positions to which they are attached if $=$ is a double bond and Y and Y' are each hydrogen if $=$ is a single bond;

$R_1$ is H or $CH_3$;

R1 is H and R2 is OH, or R2 and R3 taken together are $=O$; and

R is selected from:

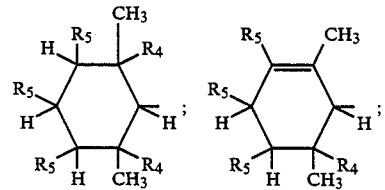

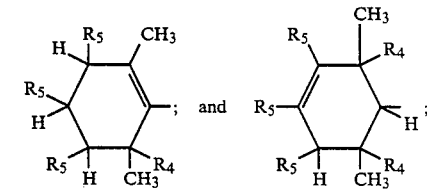

wherein
$R_4$ is H or $CH_3$, $R_5$ is H or $CH_3$, with the proviso that only one $R_5$ on the ring is $CH_3$, and when Y and Y' are H and $R_2$ and $R_3$ taken together are =O, then R is cyclohexenyl.

2. The method of claim 1 wherein said compound comprises a cyclohexyl or cyclohexenyl butenol of the structure

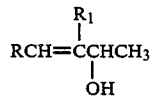

wherein R and $R_1$ are as defined above.

3. The method of claim 1 wherein said compound comprises a cyclohexyl or cyclohexenyl butanol of the structure

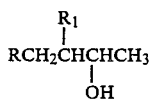

wherein R and $R_1$ are as defined above.

4. The method of claim 1 wherein said compound comprises a cyclohexyl or cyclohexenyl butenone of the structure

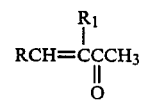

wherein R and $R_1$ are as defined above.

5. The method of claim 1 wherein said compound comprises a cyclohexenyl butanone of the structure

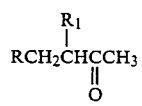

wherein R and $R_1$ are as defined above.

6. The method of claim 2 wherein said compound is selected from the group consisting of 4-(2,6,6-trimethyl-2-cyclohexen-1-yl)-3-buten-2-ol; 4-(2,6,6-trimethyl-1-cyclohexen-1-yl)-3-buten-2-ol; 3-methyl-4-(2,6,6-trimethyl-2-cyclohexen-1-yl)-3-buten-2-ol; 4-(2,4,6-trimethyl-3-cyclohexen-1-yl)-3-buten-2-ol; and 4-(2,5,6,6-tetramethyl-2-cyclohexen-1-yl)-3-buten-2-ol.

7. The method of claim 3 wherein said compound is selected from the group consisting of 4-(2,6,6-trimethylcyclohexyl)-2-butanol; 4-(2,4,6-trimethylcyclohexyl)-2-butanol; and 4-(2,6,6-trimethyl-2-cyclohexen-1-yl)-2-butanol.

8. The method of claim 4 wherein said compound is 4-(2,6,6-trimethyl-2-cyclohexen-1yl)-3-buten-2-one or 4-(2,5,6,6-tetramethyl-2-cyclohexen-1-yl)-3-buten-2-one.

9. The method of claim 5 wherein said compound is 4-(2,6,6-trimethyl-2-cyclohexen-1-yl)-2-butanone.

10. The method of claim 1 wherein said compound is in combination with a suitable carrier therefore.

11. The method of claim 1 wherein said compound is in combination with an effective amount of a insecticide or biological control agent for the Malaysian fruit fly.

* * * * *